(12) United States Patent
Kuribayashi et al.

(10) Patent No.: US 6,510,341 B1
(45) Date of Patent: Jan. 21, 2003

(54) IONTOPHORESIS DEVICE AND DRUG UNIT

(75) Inventors: Mitsuru Kuribayashi, Tsukuba (JP); Hiroyuki Maeda, Tsukuba (JP); Nobuhiro Koga, Tsukuba (JP); Naruhito Higo, Tsukuba (JP)

(73) Assignee: Hisamitsu Pharmaceutical Co., Saga (JP)

( * ) Notice: Subject to any disclaimer, the term of this patent is extended or adjusted under 35 U.S.C. 154(b) by 0 days.

(21) Appl. No.: 09/581,262
(22) PCT Filed: Dec. 21, 1998
(86) PCT No.: PCT/JP98/05776
§ 371 (c)(1), (2), (4) Date: Jun. 28, 2000
(87) PCT Pub. No.: WO99/35518
PCT Pub. Date: Jul. 8, 1999

(30) Foreign Application Priority Data
Dec. 30, 1997 (JP) ............................................. 9-369268

(51) Int. Cl.⁷ .............................................. A61B 17/20
(52) U.S. Cl. ........................ 604/20; 604/890.1; 604/501
(58) Field of Search ................................ 604/20, 890.1, 604/501

(56) References Cited

U.S. PATENT DOCUMENTS

| | | | |
|---|---|---|---|
| 4,474,570 A | * 10/1984 | Ariura et al. ................. | 604/20 |
| 5,080,646 A | * 1/1992 | Theeuwes et al. ............. | 604/20 |
| 5,250,023 A | * 10/1993 | Lee et al. ....................... | 604/20 |
| 5,310,404 A | * 5/1994 | Gyory et al. ................... | 604/20 |
| 5,837,281 A | * 11/1998 | Iga et al. ...................... | 604/304 |
| 5,894,021 A | * 4/1999 | Okabe et al. .................. | 604/20 |
| 5,993,848 A | * 11/1999 | Suzuki et al. ................. | 424/484 |

FOREIGN PATENT DOCUMENTS

| | | | | |
|---|---|---|---|---|
| EP | 1059097 A1 | * 12/2000 | ............. | A61N/1/30 |
| WO | WO 9943382 | * 9/1999 | ............. | A61N/1/30 |

* cited by examiner

*Primary Examiner*—Thomas Denion
*Assistant Examiner*—Theresa Trieu
(74) *Attorney, Agent, or Firm*—Townsend & Banta

(57) ABSTRACT

Herein disclosed is an iontophoresis device suitable for effective use of a drug supported on a drug support. A donor electrode-printed portion (6) and a reference electrode-printed portion (7) are arranged on a backing layer (4). The backing layer is provided with, at the periphery, an adhesive film (3) for fixing a pharmaceutical preparation to an application site. The both electrode-printed portions (6), (7) are electrically connected to a current-generating portion (Ia) through a conductive snap connector (Id). The drug support (14) is removably joined with a conductive layer (11) formed on the electrode on the side of the donor electrode-printed portion (6). The drug support (14) is subjected to a drug diffusion-inhibitory treatment (30).

3 Claims, 9 Drawing Sheets

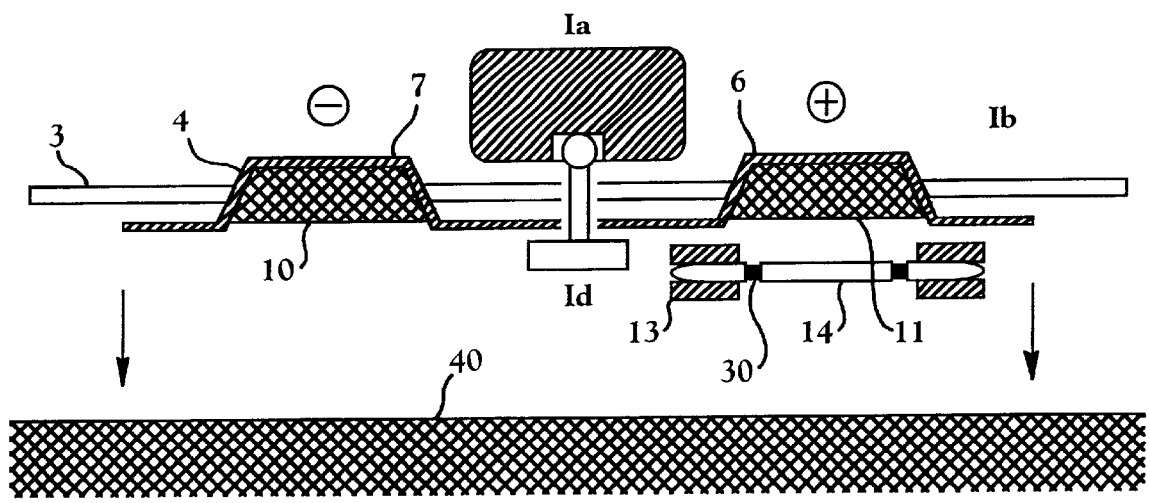
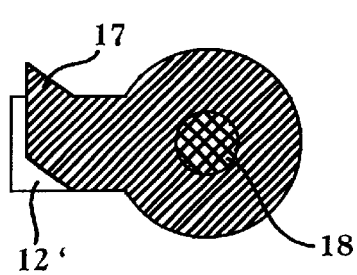
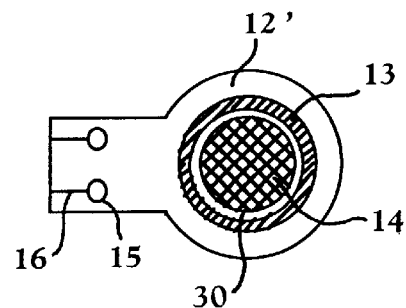
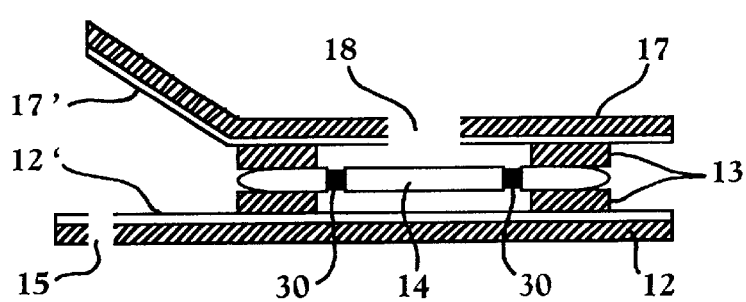
FIG. 1
FIG. 2A
FIG. 2B
FIG. 2C

IONTOPHORESIS DEVICE AND DRUG UNIT

TECHNICAL FIELD

The present invention relates to an iontophoresis device suitable for the percutaneous administration and the application through the mucous membranes and in particular to an iontophoresis device activated upon the practical use.

BACKGROUND ART

Recently, there have been developed a variety of dosage forms in the field of pharmaceutical preparations for external use and the development of dosage forms has gradually become a matter of great concern. The reason for this is as follows: The administration of a drug, which may have a local or systemic pharmacological action, through the skin or the mucous membranes has many advantages. For instance, the sustained-release effect of the drug can be expected; such administration is not greatly influenced by the metabolism due to the first-pass effect in the liver unlike the oral administration and permits the effective use of the drug; and drugs accompanied by, for instance, liver disorders can relatively safely be administered to a patient.

However the normal skin naturally has a protective effect against external stimulations and this makes the absorption and penetration of a drug through the skin relatively difficult. For this reason, in the existing circumstances, a drug is not absorbed in an amount sufficient for ensuring a satisfactory effect even if the drug is administered to a patient in a dosage form for external use. Moreover, in the administration method, which makes use of absorption routes through biological membranes other than the skin, such as mouth, rectum, oral cavity and nose as well as the sublingual route, it is difficult to penetrate into or transmit through the related biological membranes depending on the kinds of drugs and therefore, there have been known a large number of drugs having low bioavailability. Accordingly, there has been desired for the development of an absorption-promoting method, which can sufficiently enhance the permeability, penetrability and absorbency of a drug against the skin and other biological membranes, can ensure a sufficient pharmacological efficacy of the drug and is substantially free of, for instance, its local and systemic toxicity and is highly useful and safe.

As such absorption-promoting methods, there have recently been known chemically promoting methods, which make use of absorption-promoting agents, and physically promoting methods in which iontophoresis or phonophoresis techniques are employed. Among these, the iontophoresis technique has unexpectedly attracted special interest recently and has been expected as an administration method, which can solve the foregoing problems.

The iontophoresis technique is a method for the administration of a drug by applying an electric voltage to the skin or a mucous membrane to electrically induce the migration of an ionic drug and to thus administrate the drug through the skin or a mucous membrane. In general, an iontophoresis device is provided with a pair of electrode for iontophoresis, i.e., an anode and a cathode and the device is so designed that these electrodes are arranged on or attached to the skin at a predetermined distance apart from one another and an electric current generated by a current generator is guided to these electrodes to thus effect treatments of patients.

Moreover, this iontophoresis device has a structure which comprises a combination of these electrodes and a layer, which stores a drug therein, and avariety of additives for maintaining the drug efficacy are, if necessary, enclosed in the layer in addition to a predetermined amount of the effective component in order to keep a desired blood concentration in the body over a long period of time.

It has been a recent tendency to study the administration, by the iontophoresis, of polypeptide type drugs, which should be administered in a time control or intermittent type mode. Originally, the physiologically active peptides and proteins are decomposed by the digestive juice in the gastrointestinal tracts and simultaneously hydrolyzed by the hydrolases present on the wall of the digestive tract. For this reason, it is difficult to improve the absorption efficiency of these drugs and it is the leading mainstream in the medical field to administer the drugs not orally, but through injection. However, the administration through injection would give a heavy physical burden to a patient and is not always a treating method of a high compliance. Contrary to this, the iontophoresis permits the establishment of any absorption pattern by strictly controlling the electrical charging time and is an effective percutaneous absorption system which can realize an effective drug treatment, while taking into consideration the circadian rhythm, in particular, in the treatment in which an endogenous compound is supplemented. Therefore, if an iontophoresis device that permits the administration of drugs by a patient per se can be developed, it would be possibly to open the way for the home treatment.

According to the conventional studies, there have been proposed a large number of techniques relating to drug supports, which takes, into consideration, the instability of polypeptide type drugs to water and the high adsorbing ability thereof. For instance, Japanese Un-Examined Patent Publication Nos. Hei 2-218375 and Hei 2-206473 disclose drug supports capable of being electrically communicated with an electrode on the drug-administration side and capable of being brought into contact with the skin. As the drug supports of this type, there have been known, for instance, those constituted by organic members and those constituted by inorganic members. In addition, as methods for applying a drug to the drug support, there have been used, for instance, methods for coating the support with a drug or impregnating the support with a drug; or methods for applying a drug by drying or half-drying.

In these methods, however, it has been believed that drugs such as physiologically active peptides or proteins may be adsorbed on the drug support and accordingly, the rate of transdermal absorption of the drug is reduced. For this reason, there have also been proposed many techniques for solving the problem of the adsorption of drugs on the drug support. For instance, Japanese Un-Examined Patent Publication No. Hei 6-16535 discloses a technique comprising the step of coating aporousorcapillarystructuremadeof anonconductivematerial with ahigh molecular weight protein such as bovine serum albumin, human serum albumin or gelatin. Moreover, Japanese Un-Examined Patent Publication No. Hei 8-98894 discloses an interface for the iontophoresis device in which a coating layer of an ionic surfactant is formed on a drug support material. In addition, Japanese Un-Examined Patent Publication No. Hei 9-56827 discloses an interface for the iontophoresis device in which a physiologically active peptide is deposited on or applied to a thin film having an average pore size ranging from 0.1 to 15 $\mu$m, a porosity ranging from 65 to 90% and a low protein adsorptivity. Moreover, Japanese Un-Examined Patent Publication No. Hei 9-77658 discloses a technique comprising the step of applying a drug onto a hydrophobic area formed on a part of a hydrophilic film to thus give a transdermally absorbable pharmaceutical preparation.

In the conventional techniques, however, the drug support is in an exposed state and therefore, the drug is lost by any physical contact and through adsorption on the skin of a patient by any accidental touch with hands upon the application thereof, even if the drug in the dried condition is supported on the drug support. Moreover, when a drug support, which makes use of a porous hydrophilic film, is used and when a drug solution is supplied to the drug support or a drug included in the drug supportinthedriedconditionisre-dissolved, thedrugsolution diffuses from the center of the drug support to the periphery thereof due to the capillary phenomenon. Therefore, such a drug support suffers from a problem in that the drug solution moves towards an adhesive layer (for fitting the support to the skin) disposed at the periphery of the support and the amount of the drug to be used for the treatment is reduced.

On the other hand, when it is intended to incorporate, into a drug support, a drug having a high adsorbing ability and unstable to moisture, care should be taken not to lose a drug solution due to the movement thereof to other members during the term extending from the application of the drug to the completion of the drying. Otherwise the drug would be lost. It is necessary to prevent any movement of the drug towards other members during storing the drug support, or any movement of the drug towards other members during assemblage (or preparation) of a pharmaceutical preparation dissolved immediately before the practical use and during usage (during treatment), for the same reason.

In addition, it is sometimes observed that when the drug support is joined to the drug-dissolving portion, the air, which penetrates into the joint plane, would inhibit uniform dissolution of the drug and accordingly, the application of the device never ensures any sufficient drug efficacy. This would likewise be considered to be a drug loss in a wide sense and such insufficient dissolution of the drug present in the drug support would inhibit the effective use of the drug. Moreover, the electrical charging of the device is non-uniform due to the air penetration and there is sometimes observed skin stimulations upon practical use. The inventors of this invention were the first research workers to experience such a problem during studying and developing an iontophoresis device and there has never been known any prior art which refers to this problem.

Accordingly, it is an object of the present invention to provide an iontophoresis device suitable for effective use of a drug incorporated into a drug support as well as a drug unit.

DISCLOSURE OF THE INVENTION

The foregoing object of the invention can be accomplished by providing an iontophoresis device which comprises a drug-dissolving portion having a drug-activation function and a drug support subjected to a treatment for inhibiting any drug diffusion and/or a treatment for exhausting air and removably connected to the drug dissolving portion.

Thus, if the drug support is subjected to a drug diffusion-inhibitory treatment, the dissolved drug does not migrate to other members and the drug may efficiently be used. In addition, if the drug support is subjected to a treatment for exhausting any air, any air present is exhausted when the drug-dissolving portion is joined to the drug support and the drug is uniformly dissolved. Therefore, the drug can likewise efficiently be used in this case.

In this respect, the drug support can be subjected to a drug diffusion-inhibitory treatment by disposing a resin part or a thermally compressible portion at the periphery of the drug support. In addition, the air-exhausting treatment may comprise the step of forming an air vent hole at the periphery of the drug support.

Moreover, the drug support prior to the practical use is provided in the form housed in a drug unit. This drug unit is provided with members such as a drug support for accommodating a drug, a cover placed on one side of the drug support, a cover placed on the other side of the support and an adhesive for removably fixing the both covers to the drug support. These covers also serves as members for protecting the drug support and thus examples thereof usable herein are liners and caps or lids covering or put on the drug support. In addition, if necessary, the cover may be subjected to a drug adsorption-inhibitory processing or a drying agent for maintaining drugs in the dry condition may be positioned within the drug unit. Such a construction of the drug unit permits the protection of the drug support from any touch with hands and/or any physical contact immediately before the practical use. In addition, the construction also prevents any transfer of the drug to other members and can maintain the drug in its dry state. Thus, the drug support allows the effective use of the drug accommodated therein.

BRIEF DESCRIPION OF THE DRAWINGS

FIG. 1 is a diagram showing the cross sectional structure of an iontophoresis device according to the present invention upon its practical use.

FIG. 2 is a diagram showing an embodiment of a drug unit in which (a), (b) and (c) are a view of the surface, an internal view and a cross sectional view of the drug unit, respectively.

BEST MODE FOR CARRYING OUT THE INVENTION

Figure 3A:
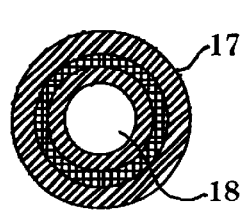
FIG. 3 is a diagram showing another embodiment of a drug unit in which (a), (b) and (c) are a view of the surface, an internal view and a cross sectional view of the drug unit, respectively.

FIG. 1 is a diagram showing the cross sectional structure of an iontophoresis device according to the present invention upon its practical use. In this figure, every part is depicted separately to make, easier, the understanding of these parts, which are in fact in a laminated relation or come in close contact with one another.

In this figure, a donor electrode-printed portion 6 is positioned on one side of a backing layer 4 and a reference electrode-printed portion 7 is positioned on the other side of the layer 4. An adhesive film 3 such as a medical adhesive tape is disposed on the periphery of the backing layer 4 for securing a pharmaceutical preparation to an application site. The both electrode-printed portions 6, 7 are connected to a current-generating portion Ia through a conductive snap connector Id. The donor electrode-printed portion 6 on the backing layer 4 is provided with a conductive layer 11 (a drug-dissolving portion) on the donor electrode side, while the reference electrode-printed portion 7 is provided with a conductive layer 10 on the reference electrode side. A drug support 14 is removably connected to the drug-dissolving portion 11. An adhesive layer 13 is formed on a part of the drug support 14, whereby the drug support 14 is fixed to the backing layer 4 or the donor electrode-printed portion 6.

The iontophoresis device having such a structure discussed above is adhered to, for instance, the skin 40 upon the practical use thereof, as shown in FIG. 1. At this stage, the drug, which is in a dry condition and supported on the drug support 14, is dissolved in the water supplied from the drug-dissolving portion 11. Since the periphery of the drug support 14 is subjected to a drug diffusion-inhibitory treatment 30, the drug remains at a desired position on the drug support 14 without causing any migration towards other members. Moreover, the air is removed from the joined region between the drug-dissolving portion 11 and the drug support 14 since the drug support 14 has been subjected to an air-exhausting treatment (not shown). Then a power supply for the current-generating portion Ia is switched on to thus put the iontophoresis device in operation.

In this respect, the drug support 14 is accommodated in the drug unit prior to the practical use as will be detailed below and thus separated from the drug-dissolving portion 11. Accordingly, even if the drug support comprises a drug (such as physiologically active peptides) whose stability to water is insufficient, it is not necessary to be anxious about decomposition of the drug with time due to the moisture present in the drug-dissolving portion.

The drug dissolved in the water supplied from the drug-dissolving portion never migrates to other members of the device since the periphery of the drug support is subjected to a drug diffusion-inhibitory treatment. In addition, any air does not penetrate into the joined region between the drug-dissolving portion and the drug support because of the air-exhausting treatment and therefore, the drug can uniformly be dissolved in the water originated from the drug-dissolving portion. Thus, the drug accommodated in the drug support can efficiently be used.

We will now explain, in detail, Examples of drug units, in which such a drug support 14 is accommodated. Detailed structures of other portions and methods for assembling the device will be described below.

EXAMPLE 1

FIG. 2 is a diagram showing an embodiment of a drug unit in which (a), (b) and (c) are a view of the surface, an internal view and a cross sectional view of the drug unit, respectively. The drug unit (Ic-1) according to this Example is formed by sandwiching a porous drug support 14 between a liner 17 on the electrode side and a liner 12 on the skin side. In this connection, the liner 17 on the electrode side is provided with a perforation for folding the liner, while the liner 12 on the skin side is provided with two insertion openings 15 for a conductive snap connector as will be explained below and a perforation 16 for pulling out the liner after the completion of the assemblage. Either of these liners herein used may be a film having low drug-adsorptive properties such as polyethyleneterephthalate. The drug is adhered to and supported by the drug support 14 by a method comprising the steps of, for instance, spraying or impregnating the support with a drug solution through an opening 18 for the application of the solution. In this respect, a cover for sealing may close the opening 18 for the application of a drug solution after the application of the drug in order to maintain the periphery of the drug support 14 under the dry condition. Moreover, Adhesive layers 13 are disposed on both sides of the periphery of the drug support in order to adhere the electrode portion to the skin and the coated pattern of the adhesive layer 13 is a stripe coating for ensuring the air exhaustion. In this connection, the side of each liner 12, 17, which comes in contact with the drug support 14, is subjected to a treatment 12', 17' with silicone in order to prevent any drug adsorption and to improve the peeling ability thereof. Moreover, the liners are also subjected to a drug diffusion-inhibitory treatment 30 to prevent any spreading of the drug solution towards the adhesive layer.

EXAMPLE 2

Figure 3B:
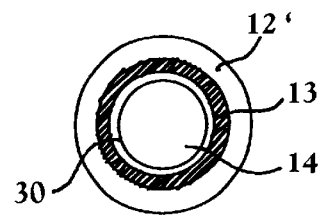
Figure 3C:
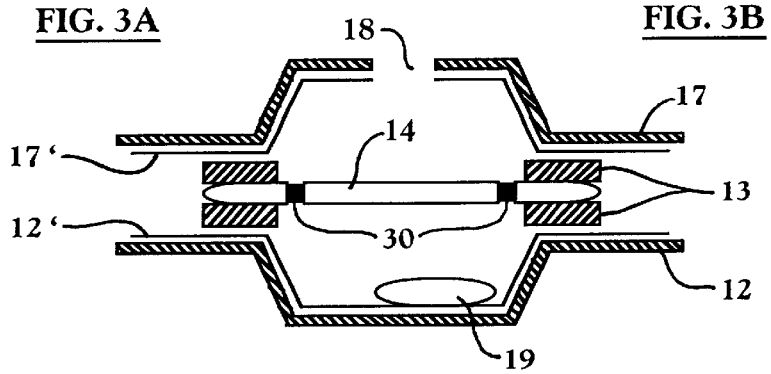

FIG. 3 is a diagram showing another embodiment of a drug unit in which (a), (b) and (c) are a view of the surface, an internal view and a cross sectional view of the drug unit, respectively. Sandwiching a porous drug support 14 between a liner 17 on the electrode side and a liner 12 on the skin side forms the drug unit (Ic-2) according to this embodiment. The liner 17 is provided with an opening 18 for the application of a drug solution. In addition, the side, of the drug support 14, of each liner 12, 17 is subjected to a treatment 12', 17' with silicone to prevent any drug adsorption and adhesive layers 13 are disposed on the both sides of the drug support 14. In this respect, Example 2 is identical to Example 1. However, Example 2 is substantially different from Example 1 in that both of the liners are fabricated and designed in such a manner that they do not come in direct contact with the drug support 14. A drying agent 19 (such as a patch type-drying agent) is disposed on the inner side of the fabricated liner 12.

EXAMPLE 3

Figure 4A:
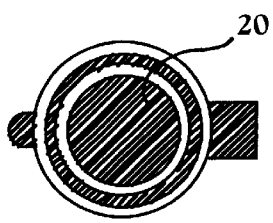
FIG. 4 is a diagram showing still another embodiment of a drug unit in which (a), (b) and (c) are a view of the surface, an internal view and a cross sectional view of the drug unit, respectively.
Figure 4B:
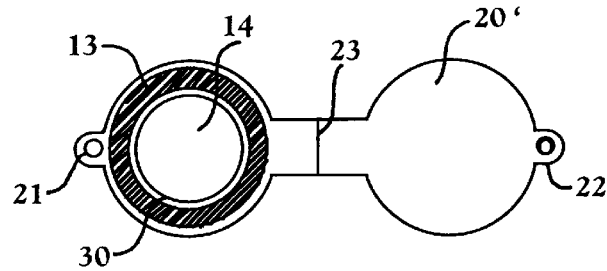
Figure 4C:
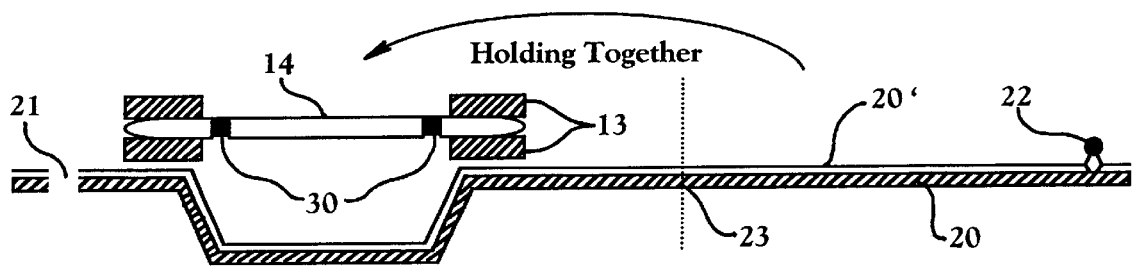

FIG. 4 is a diagram showing still another embodiment of a drug unit in which (a), (b) and (c) are a view of the surface, an internal view and a cross sectional view of the drug unit, respectively. In the drug unit (Ic-3) according to this Example, The configuration of the unit is identical to those disclosed in Examples 1 and 2 except that the structure of the liner differs from those used in Examples 1 and 2. The liner of. this Example is constituted by an integrally molded liner 20 and divided into a molded portion and a flat portion, which border across a folding axis 23. In other words, the liner is designed such that the drug support is sandwiched between the molded and flat portions upon storing the same. In addition, a fixing terminal 22 and an opening 21 for inserting the fixing terminal are formed as a member for fixing the liner after sandwiching the drug support. Moreover, the integrally molded liner 20 comprises a conventional plastic film and a dry component-containing layer 20' laminated with the film so that the interior of the drug unit is maintained in its dry condition. In principle, this Example does not require the use of any drying agent, but a drying agent may be used in combination.

EXAMPLE 4

FIG. 5 is a diagram showing a variety of embodiments of the method for subjecting a drug support to a drug diffusion-inhibitory treatment. In this Example, the drug support 14 is composed of a porous film material. In this figure, (a), (c), (e) and (g) are views of the surface of the support and (b), (d), (f) and (h) are cross sectional views thereof.

Figure 5A:
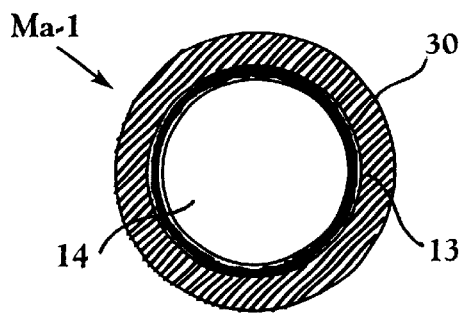
FIG. 5 is a diagram showing a variety of embodiments of the method for subjecting a drug support to a drug diffusion-inhibitory treatment, in which (a), (c), (e) and (g) are views of the surface of the support and (b), (d), (f) and (h) are cross sectional views thereof.
Figure 5B:
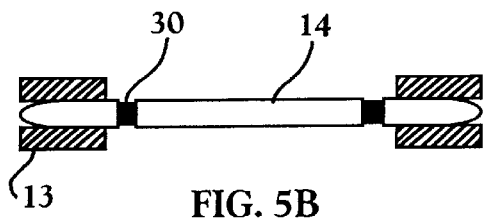
Figure 5C:
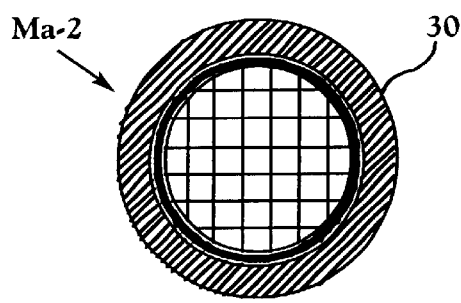
Figure 5D:
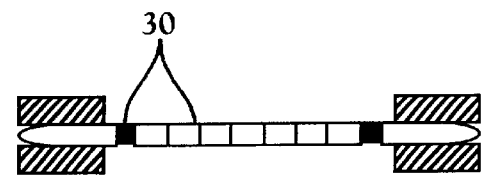

In an embodiment Ma-1, the diffusion-inhibitory treatment 30 comprises, as shown in FIGS. 5(a) and (b), the step of partially applying a thermosetting water-repellent resin (such as a silicone resin) to a region adjacent to the interior of the adhesive layer 13 of the drug support 14 or printing the region with the resin to thus close the pores.

In an embodiment Ma-2, the drug support 14 is treated by the same method described above, as shown in FIGS. 5(c) and (d). In this case, however, the drug support is further entirely subjected to a diffusion-inhibitory treatment 30 in a mesh-like pattern in order to uniformly disperse a drug solution on the drug support 14.

Figure 5E:
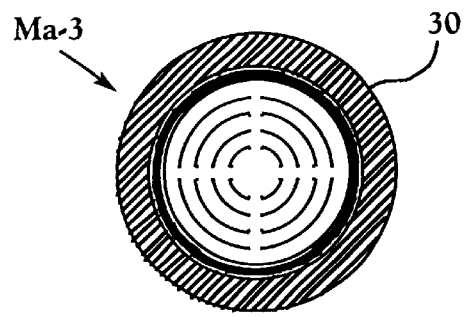
Figure 5F:
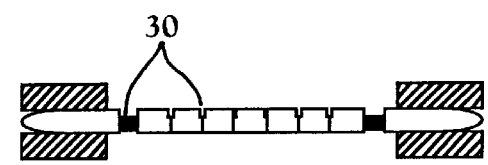

In an embodiment Ma-3, the diffusion-inhibitory treatment 30 comprises the step of partially subjecting the drug support 14 to a thermal compression treatment, as shown in FIGS. 5(e) and (f), to thus eliminate any pores of the support. In this Example, unevenness is simultaneously imparted to the porous film material during the treatment. According to this Example, any diffusion of the drug solution can be prevented by the elimination of the pores and the formation of unevenness by the thermal compression treatment.

Figure 5G:
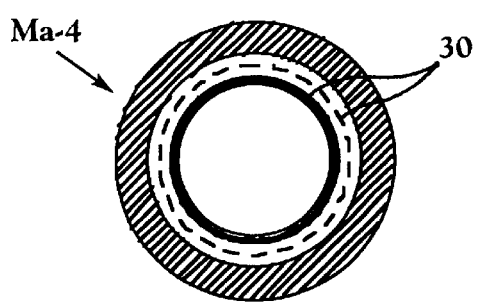
Figure 5H:
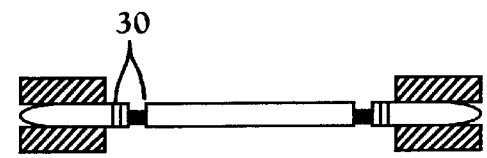

In an embodiment Ma-4, the diffusion-inhibitory treatment 30 comprises, as shown in FIGS. 5(g) and (h) the combination of a partial compression treatment of the drug support 14 and amethod comprising cutting through, for instance, a perforation. In this case, the perforation is formed on the exterior of the thermally compressed portion corresponding to a non-conductive region.

The shape and width of the pattern formed by the diffusion-inhibitory treatment 30 are not restricted to any specific one. The pattern is desirably a circular shape having a width ranging from 0.5 to 1.5 mm. In this Example, 4 embodiments of the diffusion-inhibitory treatment have been described, but the treatment is not restricted to these specific embodiments and the treating methods and the processed patterns may arbitrarily be combined or changed.

EXAMPLE 5

FIG. 6 is a diagram showing a variety of embodiments of the method for subjecting a drug support 14 and an adhesive layer 13 to an air-exhausting treatment, in which (a), (c), (e) and (g) are views of the surface of the support and adhesive layer; and (b), (d), (f) and (h) are cross sectional views thereof.

Figure 6A:
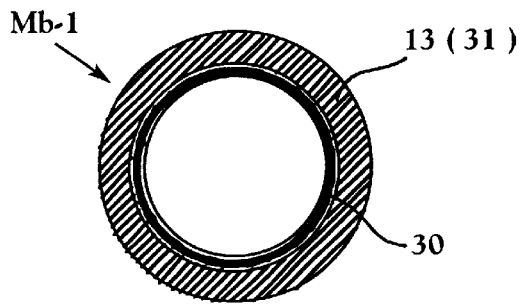
FIG. 6 is a diagram showing a variety of embodiments of the method for subjecting a drug support and an adhesive layer to an air-exhausting treatment, in which (a), (c), (e) and (g) are views of the surface of the support and (b), (d), (f) and (h) are cross sectional views thereof.
Figure 6B:
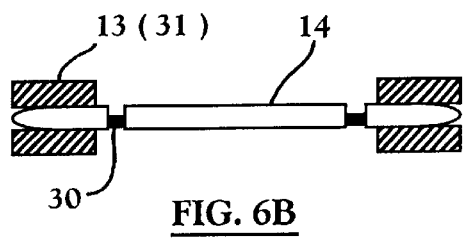

In an embodiment Mb-1, the adhesive layer 13 positioned in a region adjacent to the exterior of a region of the drug support 14 subjected to a diffusion-inhibitory treatment 30 (thermal compression) is subjected to an air-exhausting treatment 31 such as a stripe coating, as shown in FIGS. 6(a) and (b).

Figure 6C:
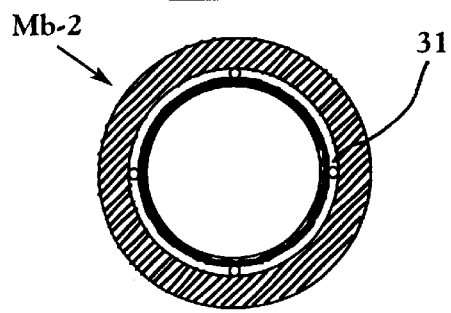
Figure 6D:
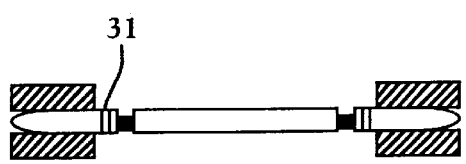

In an embodiment Mb-2, four air-exhausting holes, as regions subjected to an air-exhausting treatment 31, are formed between the region subjected to the diffusion-inhibitory treatment 30 (thermal compression) and the adhesive layer and further the adhesive layer 13 is subjected to a stripe coating treatment for air-exhaustion, as shown in FIGS. 6(c) an (d). A desired effect can be expected by forming at least two holes, as such air-exhausting holes, having a diameter of 1 mm or less.

Figure 6E:
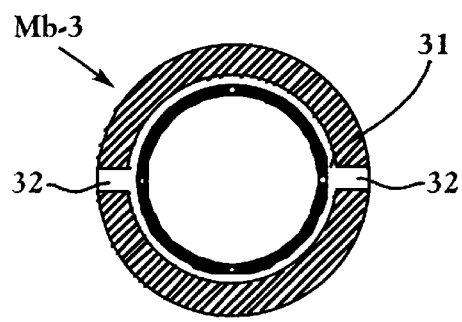
Figure 6F:
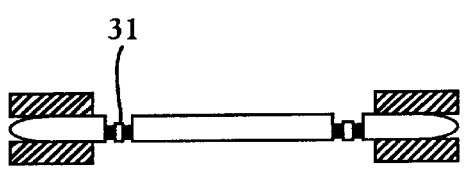

In an embodiment Mb-3, four air-exhausting holes are formed within the region subjected to the diffusion-inhibitory treatment 30 (thermal compression treatment), as regions subjected to an air-exhausting treatment 31 and uncoated portions 32 for air-exhaustion are formed on the adhesive layer 13, as shown in FIGS. 6(e) and (f).

Figure 6G:
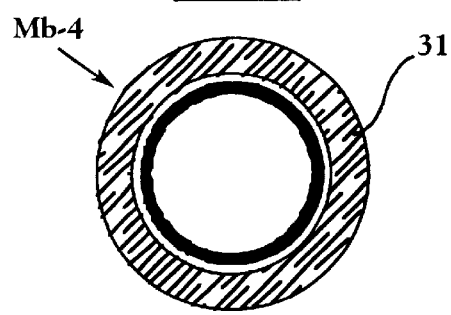
Figure 6H:

In an embodiment Mb-4, a notch is formed on the adhesive layer 13, which has been subjected to a stripe coating as an air-exhausting treatment 31, through the drug support 14, as shown in FIGS. 6(g) and (h). In this embodiment, the effect of air-exhaustion through the adhesive layer 13 is further improved. In any case, the regions subjected to the air-exhausting treatment are formed such that the conductive portion containing a drug solution is electrically isolated and therefore, there is not any possibility of causing a leakage of electricity through the regions, which have been subjected to such an air-exhausting treatment.

In case where the adhesive layer 13 is subjected to the foregoing pattern coating (intermittent coating, stripe coating, intermittent stripe coating), the width of the intermittent pattern is not restricted to any particular range insofar as a good balance between the adhesive force and air-permeability is established, but it is desirably ranges from 0.1 to 20 mm. It is also possible to make a cut such as a perforation, in addition to the foregoing methods. The shape of the cut is not restricted to any particular one. However, a circular perforation is desirably formed, which has a width ranging from 0.5 to 2 mm. In this Example, four embodiments are illustrated as a method for subjecting the drug support 14 to an air-exhausting treatment, but the present invention is not restricted to these embodiments. More specifically, the treating methods and the processed patterns may arbitrarily be combined or changed.

We will hereunder explain, in detail, materials or the like of each part of the drug unit as shown in FIGS. 2 to 6.

The adhesive layer 13 may be formed using adhesives used for forming an adhesive film 3 as will be detailed below. This layer can be formed by pattern coating (intermittent coating, stripe coating, intermittent-stripe coating) and the layer desirably has a structure, through which air easily passes. The width of the intermittent pattern formed by the pattern coating is not restricted to any particular range insofar as a good balance between the adhesive force and air-permeability is established, but it is desirably ranges from 0.1 to 20 mm.

The drug support 14 may support a drug consisting of a physiologically active substance and may be formed from any material insofar as the drug may pass through the material. In case where the drug is a physiologically active substance or a protein, a hydrophilic porous material may be used for forming the support 14 and the material can support drugs in dry states and has low adsorptivity. The hydrophilic film formed from such a hydrophilic porous material includes a thin film having high wettability by water such as a hydrophilized hydrophobic (or water-repellent) polymer thin film or a hydrophilic substance-containing hydrophilic polymer film.

Examples of hydrophilized hydrophobic polymer thin films are thin films formed from hydrophilized fluoroplastics (such as hydrophilic DURAPORE available from Millipore Company and hydrophilic poly(tetrafluoroethylene) available from Toyo Roshi Co., Ltd.), thin films such as those formed from hydrophilic polyther sulfone (such as Supor available from German Science Company) and hydrophilized cellulose derivatives (such as hydrophilized cellulose monoacetate and hydrophilized cellulose triacetate).

Examples of hydrophilic substance-containing hydrophilic polymer thin films include a variety of polymers obtained by adding appropriate surfactants and impregnating therewith and then drying, for instance, hydrophilized cellulose acetate films (such as Asymmetric Ultra Filter available from sartorius Company and cellulose acetate type ones available from Toyo Roshi Co., Ltd.), hydrophilized polycarbonate films (such as Isopore Membranes available from Nihon Millipore Ltd.), hydrophilized poly (tetrafluoroethylene) films (such as Omnipore Membranes available from Millipore Company), hydrophilized polysulfone films (such as HT Tuffryn available from Gelman Sciences Inc.) and hydrophilized nonwoven fabrics (such as films obtained by coating polyester nonwoven fabrics with cellulose acetate (e.g., coated type membranes available from Toyo Roshi Co., Ltd.)). The hydrophilic films also include, for instance, nylon films (such as BIODYNE available from Nihon PALL Ltd.).

Incidentally, drugs unstable to water should desirably be included in or adhered to the drug support in their dry state in order to improve the stability of these drugs and to inhibit any leakage and deterioration thereof. On the other hand, in case of drugs stable to water, they may be supported on the drug support in their gel-like conditions. In such a gel-like drug support, suitably used herein are water-soluble polymers and hydrogel thereof. A method for preparing such a gel-like drug support comprises the step of mixing and kneading a gelling agent such as a water-soluble polymer and a drug solution. Moreover, the electrical conductivity of the gel-like drug support can be enhanced by addition of an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate. Moreover, the kneaded mixture is formed into a product to such an extent that it has a self shape-maintainability and then spreaded into a sheet or a film. If the kneaded mixture has an insufficient self shape-maintainability, amesh-like support maybe incorporated into the gel. The thickness of the gel layer desirably ranges from 0.1 to 2 mm and particularly preferably 0.3 to 0.8 mm. If it is too thin, the gel strength is considerably low, while if it is too thick, the movement of the drug is inhibited and accordingly, the rate of drug absorption is reduced.

In the present invention, the drug unit is provided therein with a protective member, which is designed to permit the arrangement of a drying agent 19. The role of the protective member is to store a drug unstable to water in its dry state and to thus improve the storage stability thereof. Further, the protective member serves to protect the drug support from any external impact. The protective member is specifically a liner such as those described above and a product obtained by molding and processing a film. The drying agent is arranged in the drug unit without coming in close contact with the drug support.

The liners 12, 17 as the protective members may be any one insofar as they are formed from awater-impermeable material, but are desirably those capable of being processed through molding (such as thermal molding and vacuum molding). Examples of such water-impermeable materials usable herein are aluminum foils, polyester films, polypropylene films and polyethylene films as well as laminated films thereof. In addition, it is desirable to use these materials after subjecting them to an adsorption-inhibitory treatment such as a treatment with silicone or Teflon. This treatment would facilitate the peeling off thereof from the adhesive layer.

As the drying agent 19, there may be used a patch type one and this is positioned on the inside of the protective member. The drying agents are not limited to any particular one insofar as they do not adversely affect the efficacy of the drug and examples thereof preferably used herein are those having strong drying ability and strong hygroscopicity or an ability of absorbing moisture within a short period of time, such as silica gel, alumina and zeolite. Moreover, the drying agent in the form of particles or powder may be packed in, for instance, paper or nonwoven fabrics or enclosed in a container. Preferably, the drying agent or package thereof is provided with an adhesive layer for the installation thereof.

Moreover, the use of a plastic film laminated with a drying component-containing layer, as a protective member, permits the maintenance of the interior of the drug unit in the dry condition. Examples of the drying components usable herein are those, which may adversely affect the drugs (the liquefaction of the drying components due to their deliquescence) and thus cannot be used in the package of the drying agents, such as calcium chloride, magnesium sulfate, aluminum oxide and barium oxide, not to speak of the components of the drying agents listed above. Moreover, the drying component-containing layer may be a product obtained by mixing and kneading the foregoing drying components with, for instance, a thermoplastic resin and then molding the resulting blend into films and may be used alone or after laminating them with the protective member, upon the practical use. Examples of such thermoplastic resins are polyethylene, polypropylene, polycarbonate, polyamide, ethylene-vinyl acetate copolymer, ethylene-methyl acrylate copolymer, polyvinyl chloride, polystyrene, polyester terephthalate and polyvinylidene chloride. These thermoplastic resins may be used alone or in any combination.

In case where the drug is decomposed through oxidation, a deoxygenation agent may simultaneously be enclosed or incorporated into the drug unit in addition to the foregoing drying component.

Drugs usable herein are any medicine used in any therapeutic field, which is soluble or dispersible in water and, in particular, physiologically active substances having a molecular weight ranging from $1\times10^2$ to $1\times10^6$ can widely be used in the present invention. Examples of drugs are narcotics, analgesics, anorexics, anthelmintics, drugs for asthma, anticonvulsants, antidiarrheals, antineoplasticagents, drugs for Parkinson's diseases, antipruritics, sympatholytic agents, xanthine derivatives, drugs for angiocardiac diseases such as calcium channel blockers, antipyretics, β-blockers, antiarrhythmic agents, hypotensive drugs, diuretics, vasodilators for blood vessels including systemic, coronary, peripheral and cerebral vessels, drugs for hemicrania, drugs for drunkness and motion sickness, antiemetics, central nervous system stimulants, drugs for cough and common cold, decogestants, diagnostics, drugs for hormonotherapy, parasympatholytic agents, parasympathomimetic agents, psychostimulants, sedatives, tranquilizers, anti-inflammatory agents, anti-arthritic agents, anti-spasmodics, antidepressants, drugs for treating psychosis, drugs for treating dizziness, anti-anxiety agents, narcotic antagonists, carcinostatic agents, hypnotics, immunosuppressors, muscle relaxants, antiviral agents, antibiotics, anorexics, antiemetics, anti-cholinergic agents, antihistamic agents, contraceptives, antithrombotic agents, bone-absorption suppressors and osteogenesis-promoting agents. However, the present invention is not restricted to these specific drugs listed above. These drugs may be used alone or in any combination.

Specific examples of these drugs include steroids such as estradiol, progesterone, norgestrel, levonorgestrel, norethindrone, medroxy-progesterone acetate, testosterone and esters thereof; nitro group-containing compounds and derivatives such as nitroglycerin and isosorbide dinitrates, nicotine, chlorpheniramine, terfenadine, triprolidine and hydrocortisone; oxicam derivatives such as piroxicam; acetic acid or propionic acid derivatives such as indometacin, flurbiprofen, felbinac and diclofenac, ketoprofen; mucopolysaccharides such as thiomucase, buprenorphine, fentanyl, naloxone, codeine, lidocaine, dihydroergotamine, pizotyline, salbutamol and terbutaline; prostaglandins such as misoprostol, enprostil, omeprazole and imipramine; benzamides such as metoclopramine, scopolamine and clonidine; dihydropyridines such as nifedipine, verapamil, ephedrine, pindolol, metoprolol, spironolactone, nicardipine HCl and calcitriol; thiazides such as hydrochlorothiazide and flunarizine; sydnone imines such as molsidomine; sulfated polysaccharides such as heparin fractions and proteins; and peptides such as insulin and homologues thereof; calcitonins and homologues such as elcatonin, protamin and glucagone; globulins, angiotensin I, angiotensin II, angiotensin III, lypressin, vasopressin, somatostatin and homologues thereof; growth hormones and oxytocin; as well as, if necessary, pharmaceutically acceptable salts thereof with acids or bases. Preferred are, for instance, narcotics, hormones, proteins, analgesics, or other low molecular weight cations. More preferably, examples of drugs include peptides or polypeptides such as insulin, calcitonin, calcitonin-related genetic peptides, vasopressin, desmopressin, protirelin (TRH), adrenocorticotropic hormones (ACTH), luteinizing hormone-release hormones (LH-RH), growth hormone-release hormones (GRH), nerve growth factors (NGF) and other release factors, angiotensins, parathyroid hormones (PTH), luteinizing hormones (LH), serumal gonadotropin, hypophyseal hormones (such as HGH, HMG, HCG), growth hormones, somatostatin, somatomedin, glucagon, oxytocin, gastrin, secretin, endorphin, enkephalin, endothelin, cholecystokinin, neurotensin, interferon, interleukin, transferrin, erythropoietin, superoxide dismutase (SOD), filgrastim (G-CSF), vasoactive-intestinal-polypeptides (VIP), muramyl dipeptides, corticotropin, urogastroneandatrialsodiumuragoguepeptides (h-ANP). However, the present invention is not restricted to these specific drugs at all. Among these, particularly preferred are peptide hormones. It is also possible to optionally use adsorption-inhibitory agents such as benzalkonium chloride, BSA (bovine serum albumin) and monolauric acid.

In the present invention, at least one of the foregoing drugs and salts thereof may be supported on the drug support. In addition, the amount of the drug is determined depending on a particular drug in such a manner that, upon administration thereof to a patient, a predetermined effective blood concentration is maintained over an effective period of time and the size of the iontophoresis device as well as the area of the drug-delivery surface thereof are determined in proportion thereto.

We will now explain, in detail below, the structures of parts other than the drug unit detailed above.

Figure 7A:
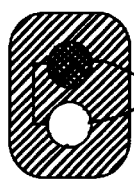
FIG. 7 is a diagram showing an embodiment of the configuration of a current-generating portion Ia, in which (a), (b) and (c) are a view of the surface, a view of the back face and a cross sectional view of the portion, respectively.
Figure 7B:
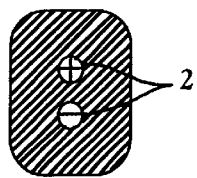
Figure 7C:
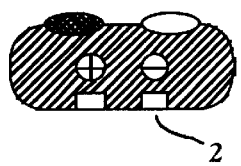
Figure 8A:
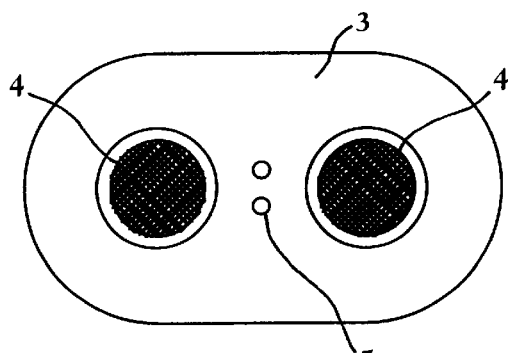
FIG. 8 is a diagram showing an embodiment of the configuration of an integrated electrode portion Ib, in which (a), (b), (c) and (d) are a view of the surface, an internal view, a view of the back face and a cross sectional view of the electrode portion, respectively.
Figure 8B:
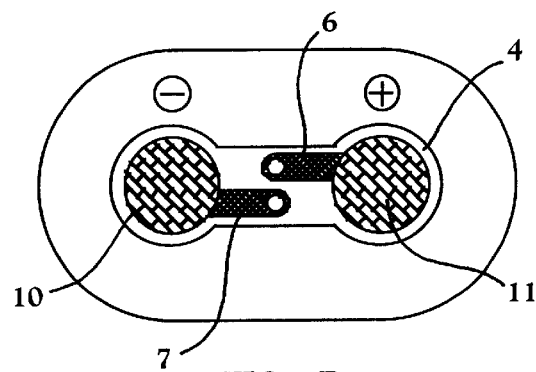
Figure 8C:
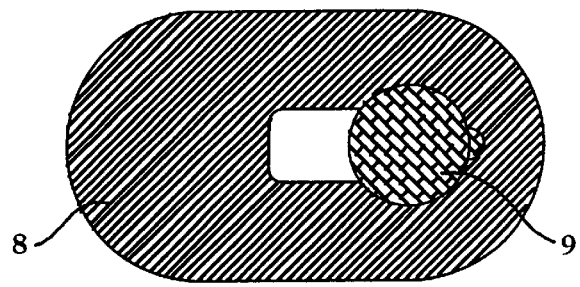
Figure 8D:
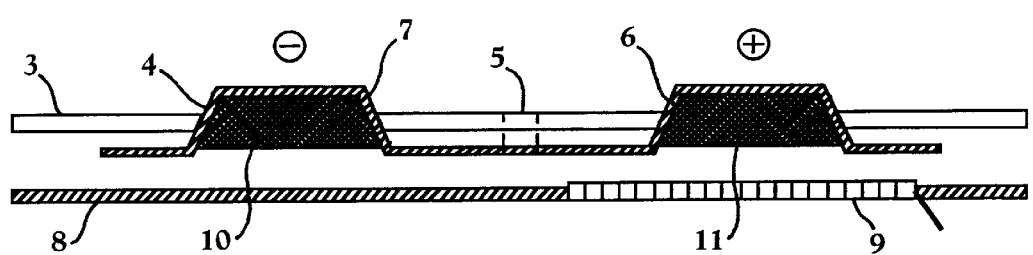

FIG. 7 is a diagram showing an embodiment of the configuration of a current-generating portion Ia, in which (a), (b) and (c) are a view of the surface, a view of the back face and a cross sectional view of the current-generating portion, respectively. The current-generating portion Ia is a plastic molded body having therein a built-in current-control circuit. A current-control switch 1 is arranged on the current-generating portion, while a female electrode terminal 2 (one each of the terminal on the sides of the anode and cathode) is arranged below the current-generating portion. This current-generating portion Ia is preferably designed such that no physical burden due to the size and weight thereof is given to a patient.

More specifically, the current-generating portion is constituted by a self-oscillator circuit provided with a built-in small-sized cell, an appropriate high voltage-generating circuit connected to the oscillator circuit and a control circuit for operating and controlling these circuits. It is also possible to incorporate a BOLUS button for temporarily increasing the injection rate for a drug into the current-generating portion. This is quite useful function when an analgesic is administered to a patient and the patient desires for a temporary increase in the dose thereof in proportion to the degree of his pains.

Moreover, the control circuit is, for instance, designed in such a manner that the circuit permits the manual on/off switching in order to allow the on-demand medication regime and the on/off switching at a period adapted for the biological circadian rhythm and the pattern at intervals of 24 hours. In addition, the control circuit may be equipped with a built-in microprocessor and therefore, the circuit permits the modification of the level of the current and the wave form such as pulses and sinusoidal waves to be applied over a predetermined time. Moreover, the control circuit may comprise a biosensor or a certain kind of feedback system for monitoring the biosignals emitted by a patient, evaluating the treating method and adjusting the amount of the drug to be administered to the patient in response to the results of the evaluation. It is also possible to incorporate one or more programs predetermined by the maker of the drug, a physician or a patient into the control circuit.

FIG. 8 is a diagram showing an embodiment of the configuration of an integrated electrode portion Ib, in which (a), (b), (c) and (d) are a view of the surface, an internal view, a view of the back face and a cross sectional view of the electrode portion, respectively. The integrated electrode portion Ib has a backing layer 4 consisting of a film of a polyester or a polyolefin such as polypropylene, or a molded body of such a film laminated with an aluminum layer. Printed electrode portions 6, 7 are arranged on the molded backing layer 4 and they are formed by printing silver (on the anode side) and silver chloride (on the cathode side). Moreover, two insertion openings 5 (one each of the opening on the sides of the anode and cathode) for conductive snap connectors are positioned on the printed electrode portion at the center of the backing layer.

Conductive layers 10, 11 are formed on the integrated electrode portion Ib in such a manner that they are adjacent to the printed electrode portions 6, 7 and the material used for forming these layers is a water-retentive material such as a nonwoven fabric or a hydrophilic polymer, which comprises an electrolyte. In this respect, the conductive layer 11 on the donor side (in this Example, the layer on the anode side) also serves as a moisture supply source for the drug accommodated in the drug unit (Ic-1), upon activation. Moreover, the conductive layers are packaged with a water-impermeable cover material 9 through easily peeled heat seal in order to prevent any moisture evaporation during storage. Further an adhesive film 3 such as a medical adhesive tape is applied onto the periphery of the backing layer 4 for the purpose of fixing the pharmaceutical preparation to a drug-application site and a liner 8 is fitted to the adhesive film during storage.

Incidentally, the integrated electrode portion Ib may have a known electrode structure. For instance, usable herein are materials such as platinum black, titanium, carbon, aluminum, iron, lead, carbon-containing conductive rubber and conductive resins, with platinum electrodes, silver electrodes, silver chloride electrodes or the like being particularly desirable.

The foregoing cover material 9 is not restricted to any particular one insofar as it is formed from a water-impermeable material. For instance, the cover material is formed from a film laminated with an aluminum layer. If a highly sealed condition by heat sealing is required, the cover material is laminated with a plurality of films such as those described above in connection with the liner or it is coated with another polymer resin. This makes the peeling off of the cover material easy. For instance, there can be used an easily peelable laminate film. It is desirable that the laminate film have a peel strength at 180 degrees of 2000 g or less.

A pressure-sensitive adhesive is used as an adhesive material for the adhesive film 3 (the adhesive layer 13 at the periphery of the drug support). Any pressure-sensitive adhesive may be used herein inasmuch as they can maintain the iontophoresis device on the surface of the skin or mucous membrane of a patient, while the device is brought into close contact therewith, they have an adhesive force sufficient for ensuring good adhesion of the drug support to the drug-dissolving portion and they are physiologically acceptable for the skin. Specific examples thereof are acrylic adhesives comprising homopolymers or copolymers of alkyl acrylates whose alkyl moiety has 4 to 18 carbon atoms, such as acrylic acid, methyl acrylate, ethyl acrylate, 2-ethylhexyl acrylate, isooctyl acrylate, decyl acrylate, lauryl acrylate and stearyl acrylate; methacrylic adhesives comprising homopolymers or copolymers of alkyl methacrylates whose alkyl moiety has 4 to 18 carbon atoms, such as methyl methacrylate, ethyl methacrylate, butyl methacrylate, 2-ethylhexyl methacrylate, isooctyl methacrylate, decyl methacrylate, lauryl methacrylate and stearyl methacrylate; silicone type adhesives such as those comprising polyorganosiloxane and polydimethyl-siloxane; and rubber type adhesives such as those comprising natural rubber, polyisobutylene,. polyvinyl ether, polyurethane, polyisobutylene, polybutadiene, styrene-butadiene copolymer, styrene-isoprene copolymer and styrene-isoprene-styrene block copolymer. Moreover, the adhesive material may, if necessary, comprise a tackifier and a softening agent.

These adhesive materials are first mixed in a mixing machine such as a kneader or a mixer and then spreaded on a support film, before the practical use. In addition, in case of the adhesive layer 13 for the periphery of the drug support, the adhesive materials are used according to, for instance, a method comprising the step of directly and partially applying them to the drug support; or a method comprising the steps of spreading them on a thermoplastic support film and then fixing the support film to the drug support through heat seal. If the drug support has insufficient flatness, the latter method is preferably used and the resulting adhesive layer permits the inhibition of any penetration of air upon activation of a drug present in the drug support. In this connection, materials for the support film usable herein may be those for the backing layer 4 as will be detailed below, but it is important to select and use materials free of any interaction with the drug and/or free of any adsorption of the drug. Moreover, in case of the adhesive film 3, preferably used herein are foams of synthetic resins, which have high gas permeability and which are quite agreeable to the touch. On the other hand, in case of the adhesive layer 13 for the periphery of the drug support, preferred are polyolefinic films having a low melting point.

A material for the backing layer 4 herein used may be an effective component-impermeable material. Examples thereof are films, sheets and foams of synthetic resins such as polyethylene, polypropylene, polyethylene terephthalate, polyvinyl chloride, polyvinylidene chloride, plasticized vinyl acetate copolymer, plasticized vinyl acetate-vinyl chloride copolymer, polyamide, cellophane, cellulose acetate, ethyl cellulose, polyester, polycarbonate, polystyrene, polyurethane, polybutadiene, polyimide, poly-acrylonitrile, polyisoprene, polystyrene derivatives, ethylene-vinyl acetate copolymer, ethylene-polyvinyl alcohol copolymer, fluoroplastics, acrylic resins and epoxy resins, which may be used alone or in the form of a laminate of at least two of them.

In addition, the films, sheets, foams or the like of these synthetic resins may be laminated with metal foils such as aluminum and tin foils; nonwoven fabrics and synthetic paper or may be covered with deposited aluminum layers and ceramic coatings. Moreover, if closed package by, for instance, heat sealing is required, they may be laminated with a heat-sealable material.

The electrode portion may be deposited on the backing layer by, for instance, a method comprising the steps of mixing an electrode material with, for instance, a print ink for electric wirings, applying the print ink to a material for the backing layer and then drying the same; a method comprising the steps of spreading an electrode material and then fixing the material to the backing layer; a method comprising the step of depositing an electrode material onto the backing layer; or a method in which the electrode portion is formed by photo-etching an electrode material applied onto the backing layer. In addition, an insulating layer may additionally be applied onto a part of the printed electrode layer, which may come in contact with the skin of a patient.

The conductive layer may simply comprise water or may comprise at least one member selected from the group consisting of soft porous materials such as ion-exchangeable polymers, foaming materials and sponge and water-absorptive polymers. Moreover, the conductive layer may comprise an electrolyte such as sodium chloride, potassium chloride, sodium carbonate, phosphoric acid or sodium citrate; or a pH-buffering agent such as acetic acid, sodium acetate, phosphoric acid, sodium phosphate, citric acid or sodium citrate, for the improvement of the electric conductivity thereof.

Specific examples of the preferably used conductive layers in general include nonwoven fabric, paper, gauze, absorbent wadding, polyethylene or polypropylene having open cells, polyvinyl acetate, porous films and foams of, for instance, polyolefin foams, polyamide foams and polyurethane, natural polysaccharides such as karaya gum, tragacanth gum, xanthane gum, starches, gum arabic, locust bean gum, gellan gum, guar gum and carrageenan; gelatin, pectin, agar, sodium alginate or polyvinyl alcohol and partially saponified products thereof; polyvinyl formal, polyvinyl methyl ether and copolymers thereof; polyvinylpyrrolidone and copolymers thereof; aqueous or water-soluble cellulose derivatives such as sodium carboxy-methyl cellulose, methyl cellulose, hydroxyethyl cellulose, hydroxymethyl cellulose, hydroxypropyl methyl cellulose, hydroxypropyl cellulose and cellulose acetate phthalate; carboxyvinyl polymer, polyacrylamide and poly-acrylamide derivatives, casein, albumin, chitin, chitosan, polyacrylic acid, sodium polyacrylate, poly-HEMA, poly-HEMA derivatives, methoxyethylene-maleic acid anhydride copolymer, N-vinyl acetamide, N-vinyl acetamide and acrylic acid and/or acrylic acid salt copolymers, as well as crosslinked products thereof, water-soluble polymers optionally plasticized with, for instance, ethylene glycol or glycerin and hydrogels thereof. However, the present invention is not restricted to these specific ones. In addition, the foregoing materials may be used in any combination of at least two of them. Moreover, it is also possible to use, if necessary, benzalkonium chloride BSA (bovine serum albumin) and adsorption-inhibitory agent such as monolauric acid.

Furthermore, the conductive layer may also comprise an ion-exchangeable polymer for the removal of ions competitive with a desired drug. Such ion-exchangeable polymers usable herein are appropriately selected from anion-exchange polymers, cation-exchange polymers and ampholytic ion-exchange polymer, depending on the ionic properties of each particular drug. In addition, the ion-exchangeable polymer may be incorporated into the conductive layer by, for instance, a method comprising the step of dispersing fine powder of an ion-exchangeable polymer in the foregoing polymer to thus form the mixture in a gel-like form or a method, which makes use of a product of such an ion-exchangeable polymer previously formed into a film, but the present invention is not restricted to these methods at all.

The capacity of the conductive layer on the donor electrode side (drug-dissolving portion) is not particularly restricted to a specific range, but depends on, for instance, the size of the electrode portion and the optimum amount of water required for dissolving a drug accommodated in the drug support, or the water content of the absorptive member of the drug-dissolving portion. In this respect, however, if the amount of water is too large, it may cause leakage of the drug-dissolving liquid, while if it is too small, the drug present in the drug support cannot completely be dissolved and the drug efficacy is correspondingly reduced. Therefore, the amount of water is desirably on the order of the maximum water absorption of the drug support. If a hydrogel is used in the drug-dissolving portion, the syneresis thereof particularly preferably ranges from 10 to 100 mg/cm$^2$. Moreover, the hydrogel should have such a gel strength that the gel is never broken during the assemblage of the device and during the application thereof to the skin and therefore, the hydrogel desirably has a gel strength ranging from 400 to 1500 g/cm$^2$.

The amount of water required for dissolving a drug present in the drug support is, in advance, controlled in the drug-dissolving portion. Thus, a precise amount of water can certainly and rapidly be supplied to the drug support at any time upon the practical use and this makes the therapeutic effect accurate. Moreover, this can also simplify the treating operations and reduce the treating time.

Figure 9A:
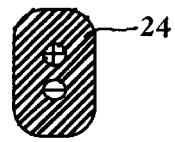
FIG. 9 is a diagram showing an embodiment of the configuration of a conductive snap connector Id, in which (a) and (b) are a view of the surface and a cross sectional view of the connector, respectively.
Figure 9B:

FIG. 9 is a diagram showing an embodiment of the configuration of a conductive snap connector Id, in which (a) and (b) are a view of the surface and a cross sectional view of the connector, respectively. This connector Id is provided with two electrode terminals 25 (male) on an electrode terminal-fixing table 24 and they are designed in such a manner that they can be connected to the electrode terminals 2 (female) of the current-generating portion Ia, after the assemblage of the device.

The current-generating portion is connected to the electrode portion such that the latter is sandwiched in between the electrode terminal on the current-generating portion side and that on the conductive snap connector side. The electrode terminal on the conductive snap connector side comes in contact with the printed electrode portion (either of the anode and cathode) of the electrode portion due to the connection. Accordingly, the current-generating portion and the electrode portion can electrically be charged and the electrical connection can thus be established.

In addition, if they are connected, while inserting the drug unit in between the current-generating portion and the electrode portion upon the assemblage of the device, the electrode terminal also serves as a means for mechanical connection for the purpose of positioning or aligning the electrode portion with the drug unit. Thus, the connection of the current-generating portion to the conductive snap connector through the electrode terminals is quite important as a means for assembling the device.

In respect of the modes of the connection of the current-generating portion to the electrode portion, the device may be operated in a cordless mode or a remote control mode using a cord. In case of the former, a small-sized current-generating portion is directly connected to the electrode portion when it is intended to carry out an easy and quick treatment. Besides, in case of the latter, the current-generating portion is connected to the electrode portion through an exclusive connecting cord when it is intended to carry out a treatment while operating the current-generating portion at hand. In this connection, connection means are fitted to the both sides of the connecting cord for the purpose of connecting the current-generating portion to the conductive snap connector. In this embodiment, electrode terminals (both anode and cathode terminals) are incorporated into a plastic molded body so that it serves to connect the terminals, to each other, of the current-generating portion and the conductive snap connector. In this respect, the connection means is not restricted to an electrode terminal and the shape and the connection mode thereof may be arbitrarily be changed. Preferably, the connection means on the conductive snap connector side has such a structure that the drug portion and the electrode portion are in line with each other and they can firmly maintain a desired arrangement.

Figure 10A:
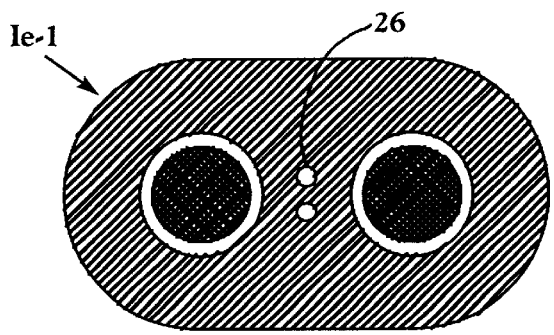
FIG. 10 is a diagram showing an embodiment of the configuration of an auxiliary stand for assemblage Ie-1, in which (a) and (b) are a view of the surface and a cross sectional view of the connector, respectively.
Figure 10B:
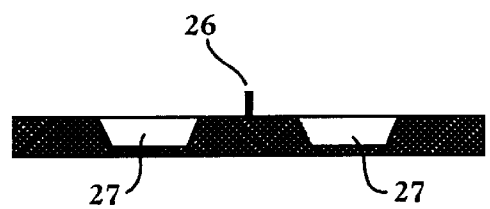

FIG. 10 is a diagram showing an embodiment of the configuration of an auxiliary stand for assemblage Ie-1, in which (a) and (b) are a view of the surface and a cross sectional view of the connector, respectively. The auxiliary stand Ie-1 for assemblage is designed in such a manner that it possesses a space 27 for accommodating the electrode portion, whose shape corresponds to that of the backing layer 4 of the electrode portion and that it has two rods 26 used for positioning upon the assemblage of the device. Materials for the auxiliary stand for assemblage are not restricted to any specific one insofar as they are selected from those capable of being shaped and/or processed, such as paper, metals, wood and plastic films (such as polypropylene, Teflon and polyvinyl chloride films), but preferred are plastic films having high shape-retention ability and a thickness of 0.5 mm or more.

This auxiliary stand for assemblage is devised to make, easy, the operations requiredwhen a patient assemble this device. In this embodiment, the stand is provided with a space 27 for accommodating the electrode portion, whose shape corresponds to that of the backing layer 4 of the electrode portion and therefore, the electrode portion can be disposed on the precise position on the auxiliary stand. The electrode-accommodating space 27 is also important in that it can prevent any damage of the electrode portion possibly encountered when the device is assembled.

In addition, the auxiliary stand may be provided with alignment rods 26. The alignment rod 26 makes it easy to align the electrode portion with the drug unit upon the assemblage of the device and is effective for eliminating the occurrence of any artificial error.

Figure 11A:
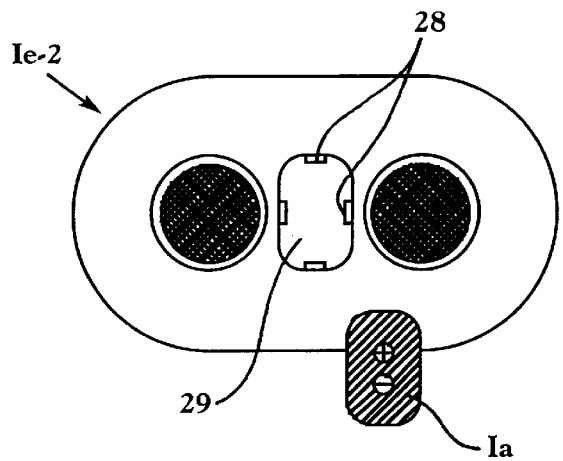
FIG. 11 is a diagram showing an embodiment of the configuration of an auxiliary stand for assemblage Ie-2, in which (a) and (b) are a view of the surface and a cross sectional view of the connector, respectively.
Figure 11B:
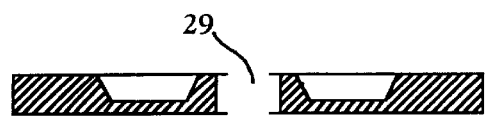

FIG. 11 is a diagram showing an embodiment of the configuration of an auxiliary stand Ie-2 for assemblage, in which (a) and (b) are a view of the surface and a cross sectional view of the connector, respectively. The auxiliary stand Ie-2 for assemblage is designed so as to have a space 29 for accommodating the current-generating portion, whose shape is in conformity with that of the current-generating portion Ia. The space 29 is provided with a means 28 for fixing the current-generating portion to the auxiliary stand Ie-2.

In this connection, the auxiliary stand for assemblage may have a structure combined with those described above depending on the shape and the procedures for assemblage of the device, and the shape thereof can further be modified. Materials for the auxiliary stand are not restricted to any specific one insofar as they are selected from those capable of being shaped and/or processed, such as paper, metals, wood and plastic films (such as polypropylene, Teflon and polyvinyl chloride films), but preferred are plastic films having a high shape-retention ability and a thickness of 0.5 mm or more.

FIG. 12 is a diagram showing an embodiment of the method for assembling an iontophoresis device, which makes use of a drug unit Ic-1 according to the embodiment 1, in which (a) shows the first half of the assembling process and (b) shows the second half of the assembling process, respectively.

Figure 12A:
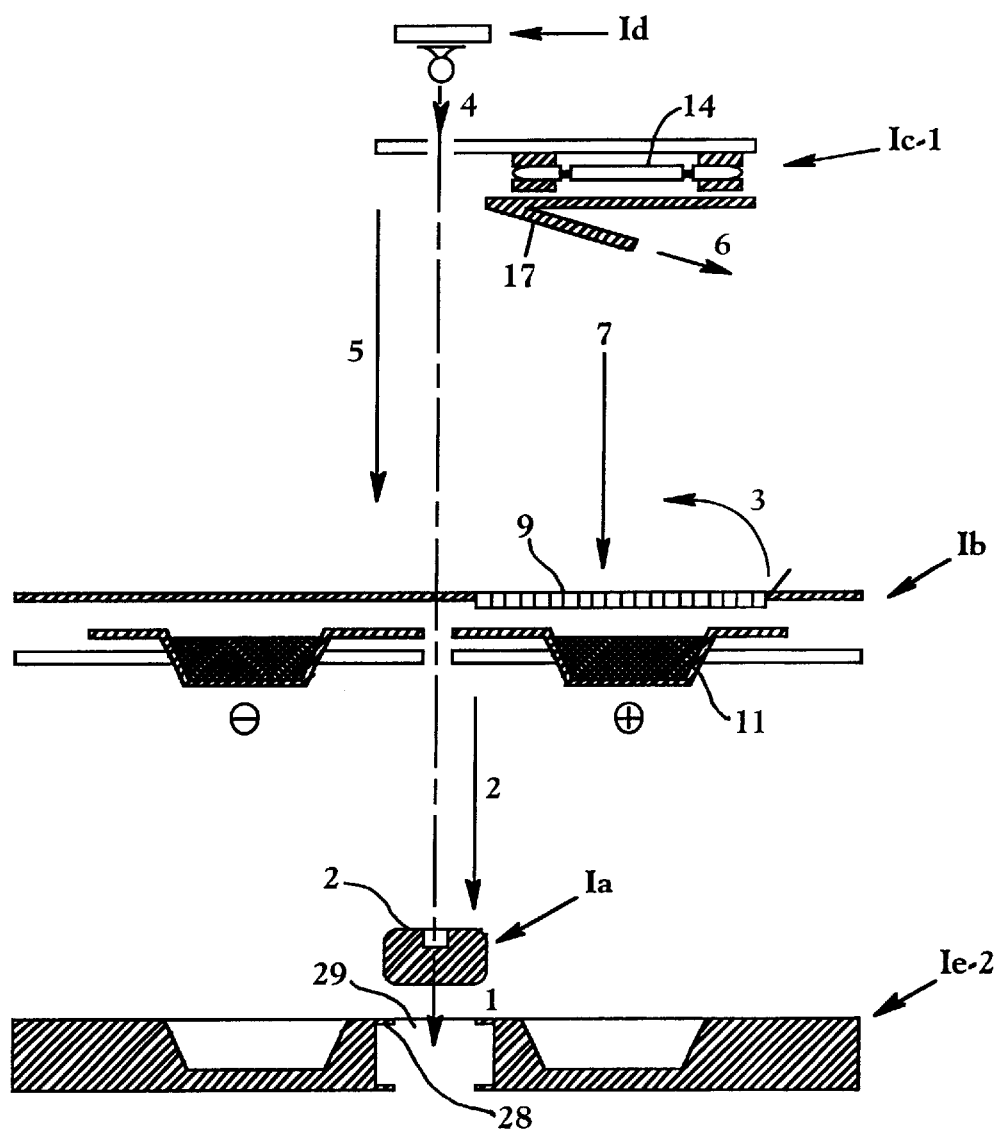
FIG. 12 is a diagram showing an embodiment of the method for assembling an iontophoresis device, which makes use of a drug unit Ic-1, in which (a) shows the first half of the assembling process and (b) shows the second half of the assembling process, respectively.

A current-generating portion Ia is incorporated into a space 29 for accommodating the current-generating portion on an auxiliary stand Ie-2 for assemblage so that an electrode terminal 2 (female) looks upward as indicated by an arrow ① in FIG. 12(a) and fixed to the stand by means 28 for fixing. Then an electrode portion Ib is disposed while it coincides with a recess of the auxiliary stand Ie-2 as indicated by an arrow ② in FIG. 12(a) and thereafter a cover material 9 of the electrode portion Ib is peeled off to thus expose a drug-dissolving portion 11 as indicated by an arrow ③ in FIG. 12(a). Subsequently, the electrode portion Ib is brought into contact with a drug unit Ic-1 using a conductive snap connector Id as indicated by arrows ④ and ⑤ in FIG. 12(a) in such a manner that they are in line with each other and thereafter a liner 17 of the drug unit Ic-1 on the electrode portion side (which has been folded along a perforation) is peeled off as indicated by an arrow ⑥ in FIG. 12(a). At the same time, a drug support 14 of the drug unit is connected to the drug-dissolving portion 11 of the integrated electrode portion as shown by an arrow ⑦ in FIG. 12(a), whereby the moisture present in the drug-dissolving portion 11 penetrates into the drug support 14 and the drug present therein is thus dissolved.

Figure 12B:
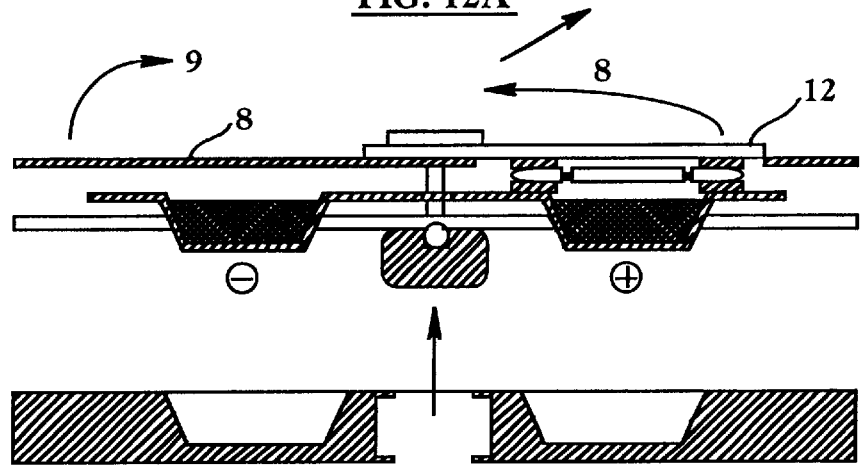

Thereafter a liner 12 of the drug unit on the skin side is pulled out from the conductive snap connector Id as indicated by an arrow ⑧ in FIG. 12(b), then a liner 8 for an adhesive film is peeled off immediately before the application of the device as indicated by an arrow ⑨ in FIG. 12(b) and finally the device is detached from the auxiliary stand. Thus, the iontophoresis device can be applied to an application site without any pre-treatment to thus initiate the treatment of a patient. The iontophoresis device according to this embodiment permits the inhibition of any movement of the drug and the drug-dissolving liquid towards the peripheral regions and the prevention of the occurrence of any non-uniform, electrically charged state due to air-admixture.

FIG. 13 is a diagram showing an embodiment of the method for assembling an iontophoresis device, which makes use of a drug unit Ic-2 according to Example 2 of the present invention, in which (a) shows the first half of the assembling process and (b) shows the second half of the assembling process, respectively.

Figure 13A:
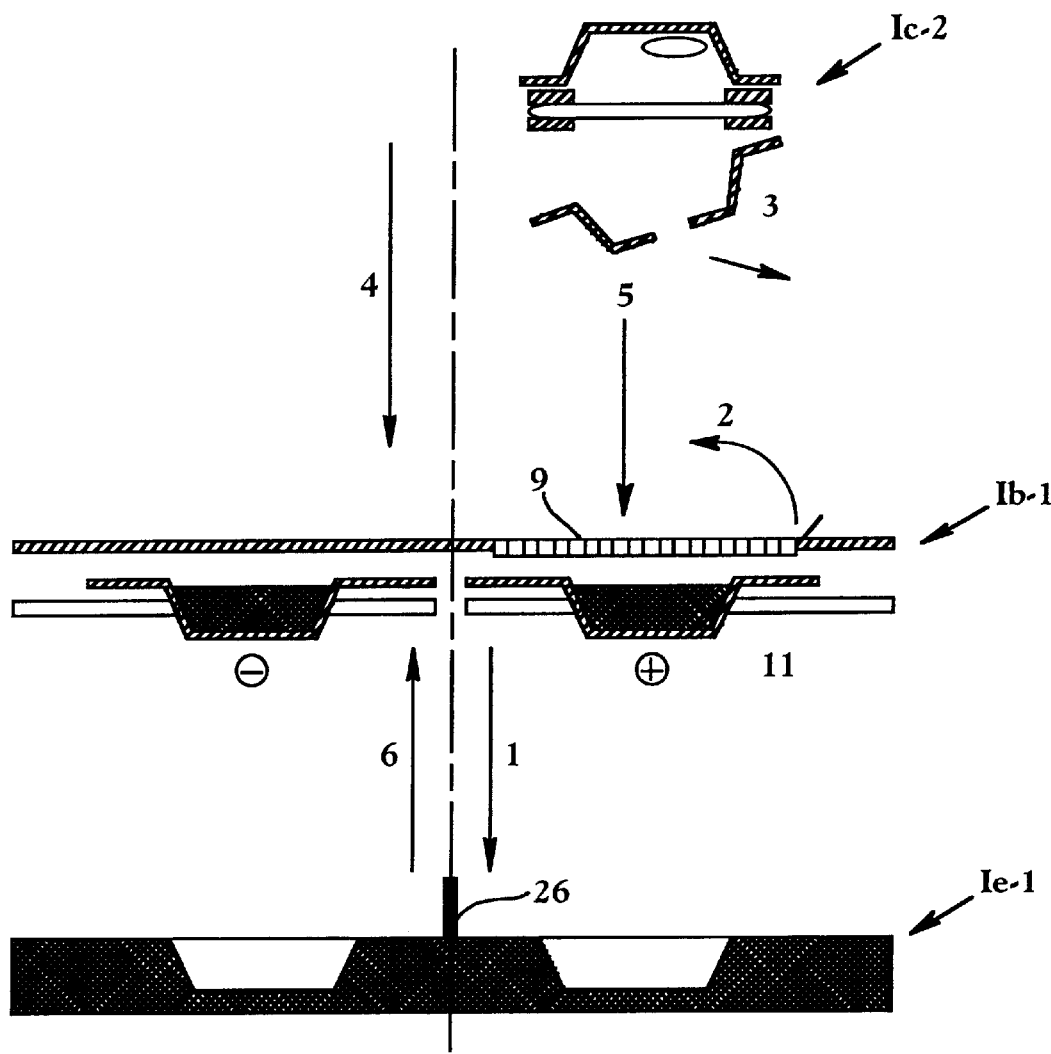
FIG. 13 is a diagram showing an embodiment of the method for assembling an iontophoresis device, which makes use of a drug unit Ic-2, in which (a) shows the first half of the assembling process and (b) shows the second half of the assembling process, respectively.

An electrode portion is positioned on an auxiliary stand Ie-1 using an alignment rod 26 of the stand as indicated by an arrow ① in FIG. 13(a) and then a cover material 9 of the electrode portion Ib-1 is peeled off to thus expose a drug-dissolving portion 11, as indicated by an arrow ② in FIG. 13(a). Further a liner 17 of the drug unit Ic-2 on the electrode portion side is peeled off, as indicated by an arrow ③ in this figure. Thereafter, the electrode portion Ib-1 is brought into contact with the drug unit Ic-2 while they are in line with one another, as indicated by an arrow ④ in the same figure to thus join the drug support 14 of the drug unit and the drug-dissolving portion 11 of the integrated electrode portion, as indicated by an arrow ⑤ in this figure. Thus, the moisture present in the drug-dissolving portion 11 penetrates into the drug support 14 and the drug present therein is correspondingly dissolved. Subsequently, the pharmaceutical preparation is removed from the auxiliary stand Ie-1.

Figure 13B:
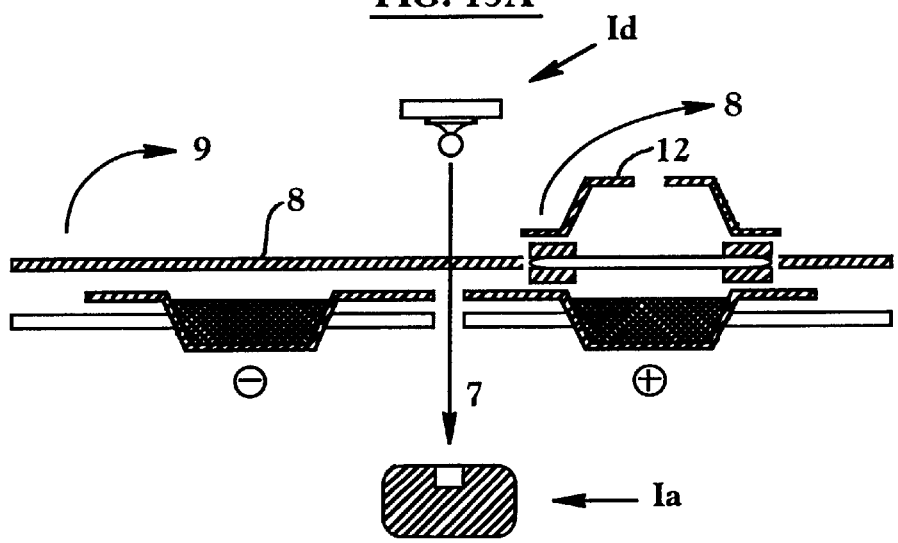

Then, after joining a conductive snap connector Id and a current-generating portion Ia as indicated by an arrow ⑦ in FIG. 13(b) and a liner 12 of the drug unit on the skin side is peeled off immediately before the application thereof as shown by an arrow ⑧ in the same figure, a liner 8 for an adhesive film is peeled off as indicated by an arrow ⑨ in this figure. Thus, the iontophoresis device can be fitted to an application site without any pre-treatment and accordingly, a treatment of a patient can be initiated. The assemblage of the device according to the procedures described above would permit the inhibition of any movement of the drug and the drug-dissolving liquid towards the peripheral regions and the prevention of the occurrence of any non-uniform, electrically charged state due to air-admixture. Moreover, the use of a molded liner likewise permits the inhibition of any adsorption of the drug solution onto the liner. Moreover, in this embodiment, a drying agent can be positioned within the drug unit and therefore, the device of the present invention permits the miniaturization of packages and the improvement in stability of the drug to be incorporated into the device.

TEST EXAMPLE 1

Experiments on Drug Adsorption on Drug Protective Member upon Assemblage of Device In this Test Example, the drug units of Examples 1 and 2 and Comparative Example 1 were inspected for the amounts of drugs adsorbed on the protective members when the drug units were activated. In this respect, the drug units and the electrode portions used herein and the device of Comparative Example 1 were as follows:

Drug Unit

Human parathyroid hormone (hPTH (1–34), 400 μg per sheet of drug support) was supported on a drug support (hydrophilic DURAPORE, average pore size: 5 μm; porosity: 70%; effective surface area: 2.5 cm$^2$) in its dry condition to thus give each drug unit.

On the other hand, the drug unit of Comparative Example 1 had a structure identical to that of Example 1, except that a protective member (liner 17 on the electrode portion side, liner 12 on the skin side) free of any adsorption-inhibitory treatment was used.

Electrode Portion

There was introduced 1.5 g of a 1.5% agar gel containing a citric acid buffering solution (33 mM, pH 5) into a conductive layer (drug-dissolving portion) adjacent to 2.5 cm$^2$ of a donor electrode (silver-printed portion) and 1.0 g of sodium chloride-containing polyvinyl alcohol (UF-250G available from Unitika, Ltd.) was introduced into areference electrode (silver chloride-printed portion) to thus give an electrode portion.

Procedures of Experiment

After assembling the drug unit and the electrode portion according to the method for assemblage described in Embodiments 1 and 2, the liner of the drug unit on the skin side was peeled off after one minute from the assemblage, the drug adsorbed on the unit was extracted with 1 ml of a 0.5 mM acetic acid buffering solution (containing 0.9% sodium chloride and 0.01% of benzalkonium chloride; pH 4) and then the amount of the drug adsorbed on the liner on the skin side was determined by the (reverse phase) high performance liquid chromatography. (n=4). Incidentally, the assemblage in Comparative Example 1 was carried out according to the assemblage method used in Example 1. The results thus obtained are summarized in the following Table 1.

TABLE 1

| | Shape of Protective Member | Material | Adsorption-Inhibitory Treatment | Amt. of Drug Adsorbed (%) |
|---|---|---|---|---|
| Example 1 | Flat Liner | Polyethylene terephthalate | Treatment with Silicone | 0.10 ± 0.13 |
| Example 2 | Molded Liner | Polypropylene | Treatment with Silicone | Not Detected |
| Comparative Example 1 | Flat Liner | Polyethylene terephthalate | — | 3.57 ± 1.89 |

The data listed in Table 1 clearly indicate that about 4% of the drug is adsorbed on the liner on the skin side in Comparative Example 1, while almost no drugs are adsorbed on the liners on the skin side upon the assemblage, in Examples 1 and 2 which make use of the protective members subjected to the adsorption-inhibitory treatment. Moreover, it was also confirmed that the use of a molded liner as a protective member permitted further reduction of the influence of the liner on the drug support. In addition, a drug solution was applied to the drug support through an opening for the application of a drug solution and then dried to examine the loss in the drug content. (Test results were not given). As a result, there was not observed any loss in the drug content for both Examples 1 and 2. In other words, a drug solution can be applied after the arrangement of a protective member and therefore, any drug loss during preparation (due to exogenous factors) can be prevented.

TEST EXAMPLE 2

Test on Inhibition of Diffusion of Drug Solution After Assemblage of Device

In this Test Example, the drug units of Example 2 and Comparative Example 2 were inspected for the amount of a drug, which diffused from a drug support to the periphery thereof when the units were activated. In this respect, the drug units and the electrode portions used herein and the device of Comparative Example 2 were as follows:

Drug Unit

The drug units of Example 2 and Comparative Example 2 used herein were identical to that used in Example 1. In this respect, however, the unit of Example 2 was subjected to a drug diffusion-inhibitory treatment while that of Comparative Example 2 was free of such a treatment.

Electrode Portion

The electrode portions used in this Test Example were the same as that used in Example 1.

Procedures of Experiment

After assembling the drug unit and the electrode portion according to the method for assemblage used in Embodiment 2, the drug unit was peeled off after 5 minutes and 15 minutes from the assemblage, followed by drying. After the drying, the drug unit (drug support) was divided into the exterior and the interior along the portion subjected to the diffusion-inhibitory treatment as a boundary to thus determine the amount of the drug diffused to the exterior of the portion subjected to the diffusion-inhibitory treatment (non-conductive portion). The amount of the drug was determined by extracting the drug adsorbed on each sample with 1 ml of a 0.5 mM acetic acid buffering solution (containing 0.9% sodium chloride and 0.01% of benzalkonium chloride; pH 4) and then subjecting the resulting extract to the (reverse phase) high performance liquid chromatography. (n=3). The results thus obtained are summarized in the following Table 2.

TABLE 2

|  | Diffusion-Inhibitory Treatment | Processing Mode | Amt. of Diffused Drug (5 min) | Amt. of Diffused Drug (15 min) |
| --- | --- | --- | --- | --- |
| Example 2 | Yes | Thermal Compression (Ma-1) | Not Detected | 0.20 ± 0.40 μg (0.05 ± 0.10%) |
| Comparative Example 2 | No | — | 200.33 ± 7.08 (55.37 ± 1.96%) | 183.99 ± 31.43 (50.85 ± 8.69%) |

It was confirmed, from the data listed in Table 2, that about 50% of the drug was found to diffuse to the non-conductive portion in Comparative Example 2 and that almost no drug diffused to the non-conductive portion and the drug was maintained within the effective area in Example 2. The results clearly indicate that, in a device free of any diffusion-inhibitory treatment, a reduced amount of the drug is practically used in the treatment of a patient after the assemblage of the device and therefore, a desired drug efficacy cannot be expected. In other words, these results suggest that the diffusion-inhibitory treatment is quite effective.

TEST EXAMPLE 3

Determination of Blood Concentration of hPTH (1–34)

In this Test Example, the drug units of Examples 1 and 2 and Comparative Example 3 were activated, then practically used and thereafter the concentrations of hPTH (1–34) in the sera were determined. In this connection, the drug units and the electrode portions herein used and the device of Comparative Example 3 were as follows:

Drug Unit

Human parathyroid hormone (hPTH (1–34), 400 μg per sheet of drug support) was supported on a drug support (hydrophilic DURAPORE, average pore size: 5 μm; porosity: 70%; effective surface area: 2.5 cm$^2$) in its dry condition to thus give each drug unit. As will be seen from Table 3, the drug units of Examples 1 and 2 hereinused were subjected to a drug diffusion-inhibitory treatment (Ma-1) and an air-exhausting treatment (Mb-1, Mb-2). On the other hand, the drug unit of Comparative Example 3 was subjected to a drug diffusion-inhibitory treatment (Ma-1), but was free of any air-exhausting treatment.

TABLE 3

|  | Shape of Protective Member | Adsorption-Inhibitory Treatment | Diffusion-Inhibitory Treatment | Air-Exhausting Treatment |
| --- | --- | --- | --- | --- |
| Example 1 | Flat Liner | Treatment with Silicone | Yes (Ma-1) | Yes (Mb-1) |
| Example 2 | Molded Liner | — | Yes (Ma-1) | Yes (Mb-2) |
| Comparative Example 3 | Flat Liner | Treatment with Silicone | Yes (Ma-1) | — |

Electrode Portion

The electrode portion herein used was identical to that used in Test Example 1.

Procedures of Experiment

SD rats (male, 6-week-old) were anesthetized with urethane and hairs on the abdominal skin was removed (hair clipper-shaver). Then each drug unit was activated according to the assemblage method used in Example 1 or 2 and subsequently the resulting device was fitted to the abdomen of the SD rat and the electrical charging thereof was initiated. The electrical charging was carried out using a 0.25 mA DC pulse current having a frequency of 40 kHz and an on/off ratio (3/7) and continued over 60 minutes. Blood samples were intrajugularly collected after the elapse of predetermined times, followed by centrifugation thereof to give each corresponding sample of the serum. The concentrations (pg/ml) of hPTH (1–34) in the sera were determined by the radioimmunoassay.

Figure 14:
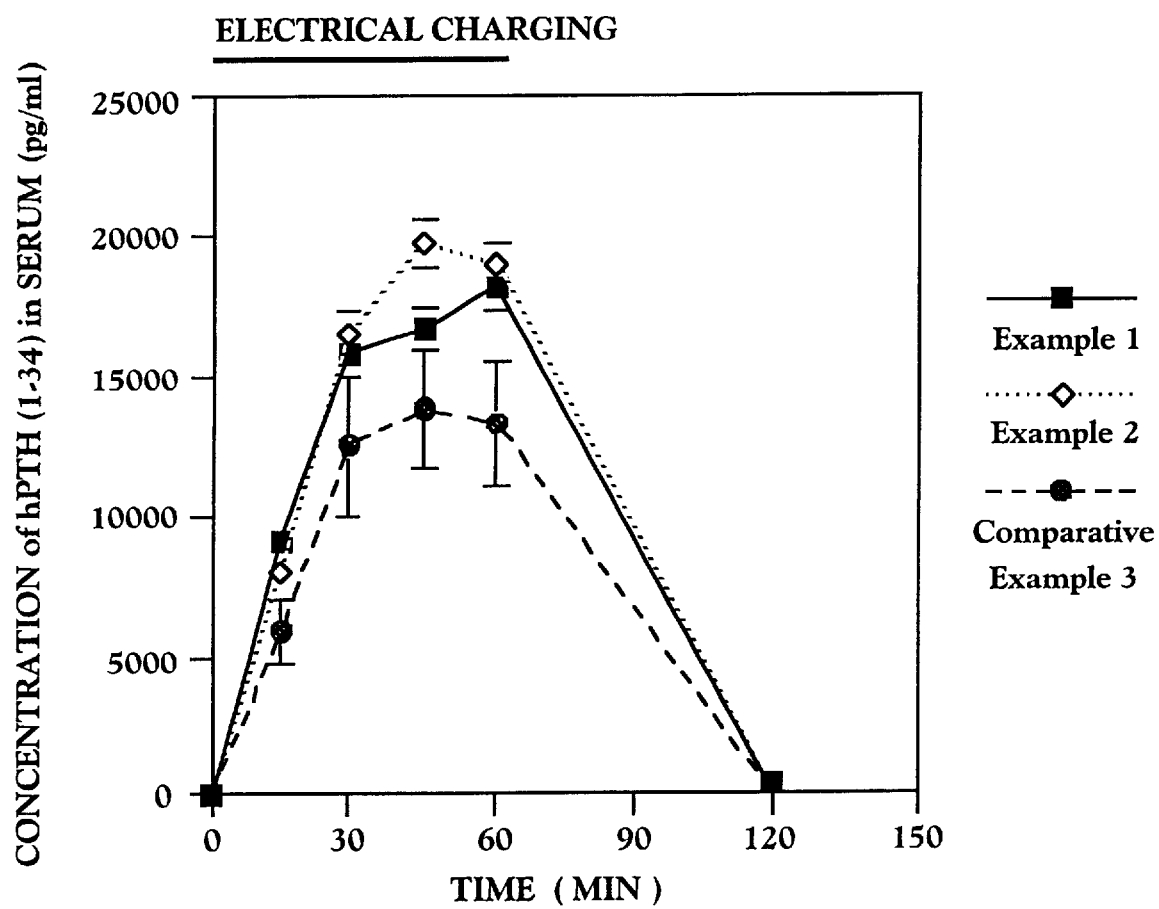
FIG. 14 is a graph showing changes, with time, of the concentration of hPTH (1–34) in the serum observed in Test Example 3.

The results thus obtained are plotted on FIG. 14 and FIG. 14 is accordingly a graph showing changes, with time, of the concentration of hPTH (1–34) in the serum observed in Test Example 3. (n=4). When the samples of this Test Example were activated, it was confirmed, in Examples 1 and 2, that the air in the device was removed and the drug-dissolving portion was evenly and uniformly brought into contact with the drug support. On the other hand, air remained in the device and it was never removed even when the device was applied to the skin, in the device of Comparative Example. The experimental results obtained using these samples indicate that the blood concentration observed in Comparative Example 3 is generally lower than those observed in Examples 1 and 2 and widely varies. In other words, it would be concluded that the blood concentration is greatly affected by the presence of air in the device. Accordingly, these results clearly suggest that the air-exhausting treatment is quite effective.

As has been discussed above in detail, the iontophoresis device according to the present invention comprises a drug support subjected to a drug solution-diffusion-inhibitory treatment and therefore, the device suitably permits the prevention of any drug loss during producing, storing, assembling and using (treating a patient) the device. The device accordingly permits the reduction of any possibility of producing substandard products during manufacture, the improvement of the drug in the long-term stability during storage and the inhibition of any leakage of a drug solution and/or any migration thereof during application. Moreover, the drug unit is subjected to an air-exhausting treatment as a means for eliminating any puddle of air in the device encountered when the device is assembled and therefore, the device allows the uniform dissolution of the drug and the uniform electrical charging of the device. Further, the device is designed in such a manner that a drying component may be disposed within the drug unit and accordingly, the long-term stability of the drug can be improved and the manufacturing process can be simplified. The foregoing indicates that the iontophoresis device according to the present invention permits accurate supply of water required for the dissolution of the drug to the drug support, which has been stored under highly stable environment and also permits the prevention of any loss of the resulting drug solution. Consequently, the device of the present invention has high biological availability.

Industrial Applicability

The iontophoresis device and the drug unit according to the present invention are useful for effective use of a drug incorporated into a drug support and are suitably used for iontophoresis in the medical field.

What is claimed is:

1. An iontophoresis device comprising a drug-dissolving portion having a function of activating a drug; and a drug unit, which is subjected to at least one treatment selected from a drug diffusion-inhibitory treatment and an air-exhausting treatment, having a drug support removably joined with the drug-dissolving portion.

2. The iontophoresis device according to claim 1, wherein the drug diffusion-inhibitory treatment includes a resin member and/or a thermally compressed portion disposed at the periphery of the drug support.

3. The iontophoresis device according to claim 1, wherein the air-exhausting treatment is to form an air vent hole at the periphery of the drug support.

* * * * *